United States Patent [19] [11] Patent Number: 4,847,200
Wolfe et al. [45] Date of Patent: Jul. 11, 1989

[54] BIOSYNTHESIS OF UNNATURAL CEPHALOSPORINS

[75] Inventors: Saul Wolfe, Kingston; Donald Westlake; Susan Jensen, both of Edmonton, all of Canada

[73] Assignee: Queen's University at Kingston, Kingston, Canada

[21] Appl. No.: 903,659

[22] Filed: Sep. 5, 1986

Related U.S. Application Data

[63] Continuation-in-part of Ser. No. 554,982, Nov. 25, 1983, abandoned.

[51] Int. Cl.⁴ .................. C12P 37/00; C12P 35/00
[52] U.S. Cl. ........................ 435/43; 435/47; 435/169; 435/886
[58] Field of Search ............ 435/43, 47, 119, 169, 435/183, 886, 48, 49

[56] References Cited

U.S. PATENT DOCUMENTS

| | | | |
|---|---|---|---|
| 3,436,310 | 4/1969 | Arnold et al. | 435/47 |
| 3,658,649 | 4/1972 | Arnold et al. | 435/47 |
| 3,979,260 | 9/1976 | Nakao et al. | 435/47 |
| 4,075,061 | 2/1978 | Fleming et al. | 435/47 |
| 4,178,210 | 12/1979 | Demain et al. | 435/47 |
| 4,283,492 | 8/1981 | Imanaka et al. | 435/47 |
| 4,307,192 | 12/1981 | Demain et al. | 435/47 |
| 4,414,328 | 11/1983 | Imanaka et al. | 435/47 |
| 4,506,014 | 3/1985 | Esser et al. | 435/172.3 |
| 4,510,246 | 4/1985 | Wolfe et al. | 435/47 |
| 4,536,476 | 8/1985 | Wolfe | 435/183 |

FOREIGN PATENT DOCUMENTS

| | | | |
|---|---|---|---|
| 0102216 | 7/1984 | European Pat. Off. | 435/43 |
| 0260778 | 3/1988 | European Pat. Off. | 435/43 |
| 0110394 | 8/1979 | Japan | 435/43 |

OTHER PUBLICATIONS

Jensen, S. E. et al., J. of Antibiotics, vol. 35, pp. 1351–1360 (1982).
Jensen, S. E. et al., Int. Cong. for Microbio. (13th), p. 121, #P42:4 (1982).
Jensen, S. E. et al., J. of Antibiotics, vol. 35, pp. 483–490, 1026–1032 (1982).
Jensen, S. E. et al., Antimicrobial Agents and Chemotherapy, vol. 24, pp. 307–312 (9–1983).
Iwanatsu, K. et al., J. of Antibiotics, vol. 36, pp. 229–241 (3–1983).
Jensen, S. E. et al., Can. J. Microbiol., vol. 29, pp. 1526–1531 (1983).
Kupaki, J. et al., Con. J. Microbiol., vol. 29, pp. 488–496 (1983).
Wolfe, S. et al., Science, vol. 226, pp. 1386–1392 (12–1984), Review, Not Prior Art.
Jensen, S. E. et al., Can. J. Chem., vol. 62, pp. 2712–2720 (12–1984), Not Prior Art.
Bowers, R. J. et al., Biochem. Biophys, Res. Comm., vol. 120, pp. 607–613 (4–1984), Not Prior Art.
Shields, J. E. et al., Helvetica Chimica Acta, vol. 67, pp. 870–875 (1984), Not Prior Art.

*Primary Examiner*—Charles F. Warren
*Assistant Examiner*—M. M. Schafer
*Attorney, Agent, or Firm*—Richard J. Hicks

[57] ABSTRACT

A process for producing unnatural penicillins and cephalosporin derivatives thereof in which peptide analogs of ACV in which the L-α-aminodipyl moiety is replaced by L-S-carboxymethyl cysteine or other obvious substituents, are reacted with cyclase, epimerase, ring expansion and hydroxylase enzymes isolated from a cell free extract of a prokaryotic organism such as S. clavuligerus. The product depends upon the presence or absence of co-factors such as ferrous ion, α-ketoglutarate, and ascorbate. In an alternative embodiment, a penicillin analog having the formula:

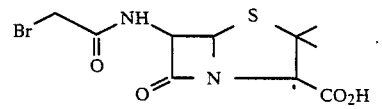

may be reduced with L-cysteine to produce an analog of isopenicillin N which may be reacted with the enzyme reagent to produce the desired penicillin or cephalosporin.

14 Claims, No Drawings

BIOSYNTHESIS OF UNNATURAL CEPHALOSPORINS

RELATION TO OTHER APPLICATIONS

This application is a continuation-in-part of our earlier filed application Ser. No. 554,982, filed Nov. 25, 1983 and now abandoned.

BACKGROUND OF THE INVENTION

1. Field of the Invention

This invention related to novel processes for the production of unnatural penicillins anc cephalosporin derivatives thereof.

2. The Prior Art

It has been reported (Journal of Antibiotics 29, 1258 (1976) RIT2214, "A New Biosynthetic Pencillin Produced by a Mutant of Cephalosporium Acremonium") that a mutant of C. acremonium produces a compound having the formula

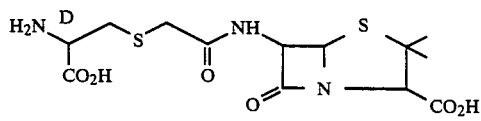

when the medium is supplemented with L-S-Carboxymethyl cysteine

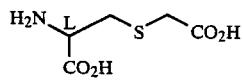

Compound (1) is a Penicillin N analog by virtue of its D-S-carboxymethyl cysteine side chain and is more active in vivo than ampicillin. It may also be synthesized from the reaction of a penicillin

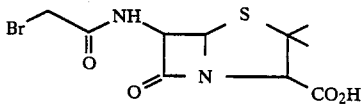

with D cysteine. Penicillin (3) may be prepared, on an industrial scale, by reaction of 6-aminopenicillanic acid (6-APA):

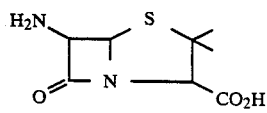

with bromoacetyl chloride

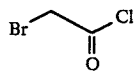

These processes are not, however, believed to be commercially viable as the mutant which produces compound (1) is not sufficiently stable for industrial use; the process which produces compound (1) following addition of (2) to the medium may also produce other penicillins and cephalosporins which are difficult to separate; and further the chemical synthesis requires the use of relatively expensive (Ca $50/gram) D-cysteine as opposed to L-cysteine (Ca $50/kilogram). It is also known (Biochemical Journal 179, No. 1, April 1979 "Biosynthesis of a 7-methoxycephalosporin") that a cell free preparation of S. clavuligerus converts the cephalosporin compound:

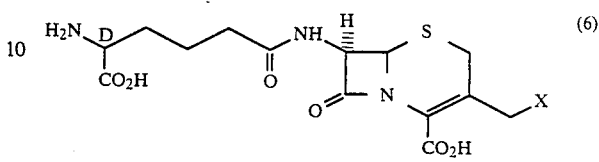

into the cephamycin:

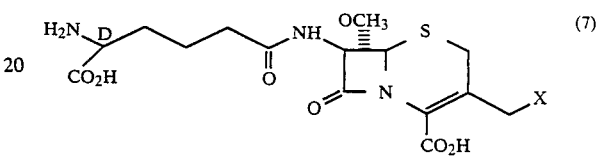

It is also known (Journal of Antibiotics 36, 229, (1983) "Synthesis and Biological Activity of 7β-(2-Amino-2-carboxy)-Ethylthioacetamido-7-α-Methoxycephalosporin Derivatives") that cephalosporins

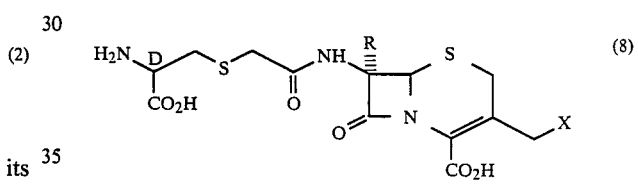

where R=H, OCH₃, having a D-S-carboxymethyl-cysteine side chain, have a high order of antibacterial activity in vivo. Such cephalosporins are, however, difficult to synthesize and require a multistep process beginning with a natural product, in addition to requiring a process for D-carboxymethylcysteine.

In our earlier filed application for Letters Patent of the United States, Ser. No. 410,302, now U.S. Pat. No. 4,510,246, and Ser. No. 507,852, now U.S. Pat. No. 4,536,476, there is described a biological process using three enzymes (cyclase, epimerase, and ring expansion enzymes) derived from S. clavuligerus or other prokaryotic organisms such as S. cattleya and S. lipmanii, which sequentially cyclizes ACV (L-Aminoadipyl-L-cysteinyl-D-valine)

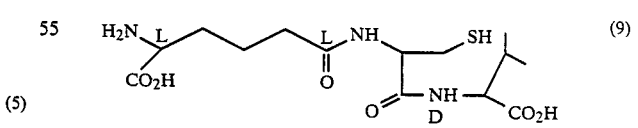

to isopenicillin-N:

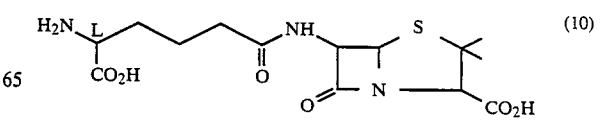

which is then epimerized to penicillin N

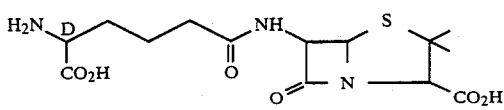

and finally ring expanded to desacetoxycephalosporin C

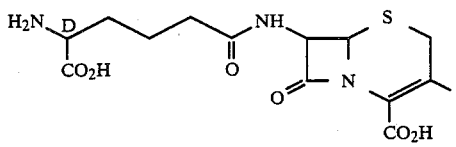

The prokaryotic β-lactam producing organisms *S. clavuligerus, S. cattleya* and *S. lipmanii* referred to above are publically available from either the American Type Culture Collection, Rockville, Md., or Northern Regional Research Laboratory, Peoria, Ill., under the following accession numbers:

|  | ATTC | NRRL |
|---|---|---|
| S. clavuligerus | 27064 | 3585 |
| S. cattleya | 39203 | 8057 |
| S. lipmanii | 27357 | 8584 |

SUMMARY OF THE INVENTION

We have also now found that the 3-enzyme mixture previously described also contains a 4th enzyme called hydroxylase which has the same co-factor requirements as the ring expansion enzyme and converts desacetoxycephalosporin C to desacetylcephalosporin C

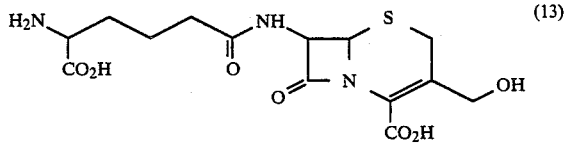

with longer reaction times. It is known that (13) can be converted chemically to compounds of the general formula

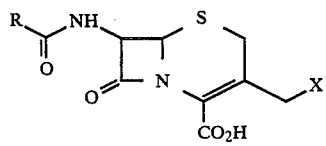

We have now also discovered that the peptide analogs (15) of ACV in which the L-α-aminoadipyl moiety is replaced by L-S-carboxymethylcysteine or other obvious sustituents therefor

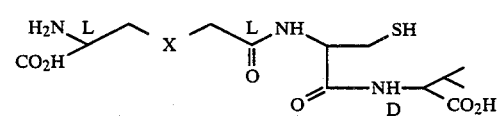

where X=S, SO, $SO_2$, O, NH, NR, PO, PR, Se, SeO or $SeO_2$ and R=alkyl or aryl are at least 50% as active as ACV as substrates for each of the *S. clavuligerus* enzymes. For convenience, analog 15 where X=S will be referred to hereinafter as S.C.V. Thus S.C.V. (15) may be converted to the analog (16) of isopenicillin N

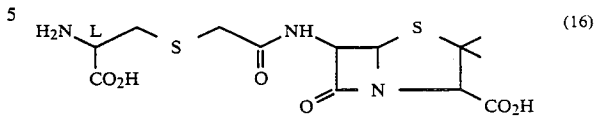

which in turn may be epimerized to (1) which in turn may be ring expanded to the D-S-carboxymethylcysteine analog (17) of Cephalexin ® (18)

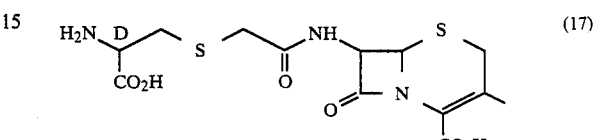

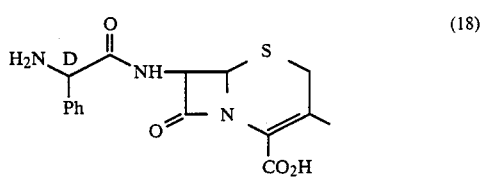

and hydroxylated to the immediate precursor (19) of the cephalosporin (8).

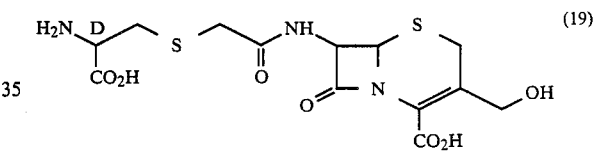

Thus, starting with (15), addition of ferrous ion, ascorbate and dithiothreitol to the reaction mixture containing the enzyme system described in the above noted U.S. patent applications (without any purification thereof) leads to (16) and thence to (1). Alternatively penicillin (3) may be reacted with relatively low cost L-cysteine so as to produce (16) which may be reacted wih the crude enzyme system to produce (1) directly, with no co-factors necessary.

To obtain (17) from (16) it is necessary to supplement the crude enzyme system with ascorbate, ferrous ion and α-ketoglutarate, the essential co-factors for the ring expansion reaction. The same co-factors are required to obtain (19) from (16). From (19) a combination of know chemical and microbiological techniques (vide Biochem. J. No. 7 1979, supra) will lead to any cephamycin with the D-S-carboxymethylcysteine side chain.

Cephalexin ® (18) is the desacetoxycephalosporin C analog of ampicillin (20).

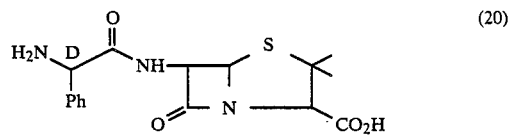

which is, of course, a highly successful commercial antibiotic compound. Cephalexin ® (18) is also an orally effective cephalosporin antibotic. As penicillin (1) with the D-S-carboxymethylcysteine side chain is more active than ampicillin, it is believed that (17) is likewise more active than Cephalexin® (18), and is therefore an effective orally absorbed antibiotic.

It will be appreciated by those skilled in the art that while the cyclase enzyme converts the natural substrate δ(L-α aminoadipyl)-L-cysterinyl-D-valine into isopenicillin N in the presence of the necessary co-factors, it will also accept, as substrate, a variety of modified tripeptides such as:

| | |
|---|---|
| DLD-ACV | AC-isoleucine |
| adipyl-CV | AC-alloisoleucine |
| phenlacetyl-CV | AC-aminobutyrate |
| carboxymethylcysteinyl-CV | | while epimerase enzyme converts the natural substrate isopenicillin N into penicillin N in a reversible reaction which does not require any co-factors, epimerase will also accept as substrate:

| | |
|---|---|
| AC-alloisoleucine | |
| AC-isoleucine | derived analogs of isopenicillin N |
| AC-aminobutyrate | | while expandase enzyme converts the natural substrate penicillin N into desacetoxycephalosporin C in the presence of ascorbate, ferrous ions and α-ketoglutarateas necessary co-factors, expandase will also accept as substrate:

| | |
|---|---|
| AC-alloisoleucine | |
| AC-isoleucine | derived analogs of penicillin N |
| AC-aminobutyrate | |

Similarly, while hydroxylase enzyme converts the natural substrate desacetoxycephalosporin C into desacetylcephalosporin C in the presence of ascorbate, ferrous ions and α-ketoglutarate as necessary co-factors, the hydroxylase enzyme will also accept as substrate the D-carboxymethylcysteinyl analog of desacetoxycephalosporin C.

STATEMENT OF THE INVENTION

Thus, by one aspect of the invention there is provided a process for producing penicillins of the formula: formula:

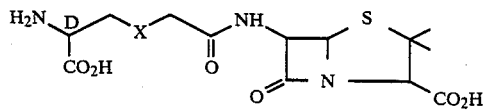

where X=S, SO, $SO_2$, O, NH, NR, PO, PR, Se, SeO or $SeO_2$ and R=alkyl or aryl which comprises reacting a peptide starting material having the formula:

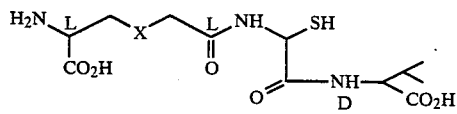

where X and R are as above defined with cyclase and epimerase isolated from a cell free extract of a prokaryotic organism for sufficient time and in the presence of sufficient co-factors to produce said penicillin.

By another aspect of the invention there is provided a process for producing analogs of penicillin-N having the formula

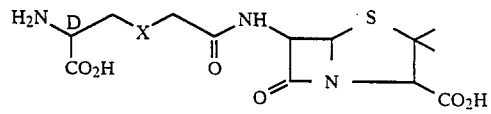

where X=S, SO, $SO_2$, O, NH, NR, PO, PR, Se, SeO or $SeO_2$ and R=alkyl or aryl comprising reacting an analog of isopenicillin-N having the formula

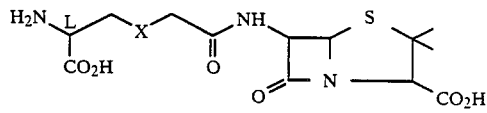

where X=S, SO, $SO_2$, O, NH, NR, PO, PR, Se, SeO or $SeO_2$ and R=alkyl or aryl with epimerase isolated from a cell free extract of a prokaryotic organism.

By yet another aspect of the invention there is provided a process for producing δ-(L-carboxymethyl cysteinyl)-L-Cysteinyl-D-valine and dimers thereof comprising (a) partially protecting amino and α carboxymethyl cysteinyl groups in L-carboxymethyl cysteine by addition of protecting groups; (b) forming a fully protected tripeptide by coupling said partially protected L-carboxymethyl cysteine with partially protected L-cysteinyl-D-valine; (c) detrytilating said fully protected tripeptide by reaction with iodine; and (d) completely deprotecting said tripeptide by treatment of detrytilated product with formic acid so as to produce δ-(L-carboxymethyl cysteinyl)-L-cysteinyl-D-valine disulfide.

DESCRIPTION OF THE PREFERRED EMBODIMENTS

In the following description reference will be made particularly to the conversion of S.C.V. (15) to analogs of penicillin-N and thence to the cephalosporin analogs thereof, which compounds are useful as antibiotics as such. It will be appreciated, however, that the biochemical techniques of the present invention are equally applicable to other starting materials and it is within the purview of the present invention to substitute the δ-(L-carboxymethyl cysteinyl) moiety in the preferred S.C.V. starting material so as to produce analogous penicillins and cephalosporins which are also useful as antibiotics per se or as starting materials for other antibiotics. Thus the general formula for the peptide analogs 15 may be regarded as having the general formula (15)

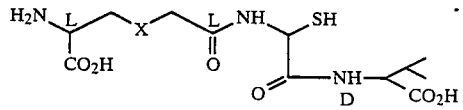

where X=S, SO, $SO_2$, O, NH, NR, PO, PR, Se, SeO or $SeO_2$ and R=alkyl or aryl.

Preparation of δ-(L-carboxymethyl cysteinyl)-L-cysteinyl-D-valine may be accomplished in accordance with the following schematic sequence:

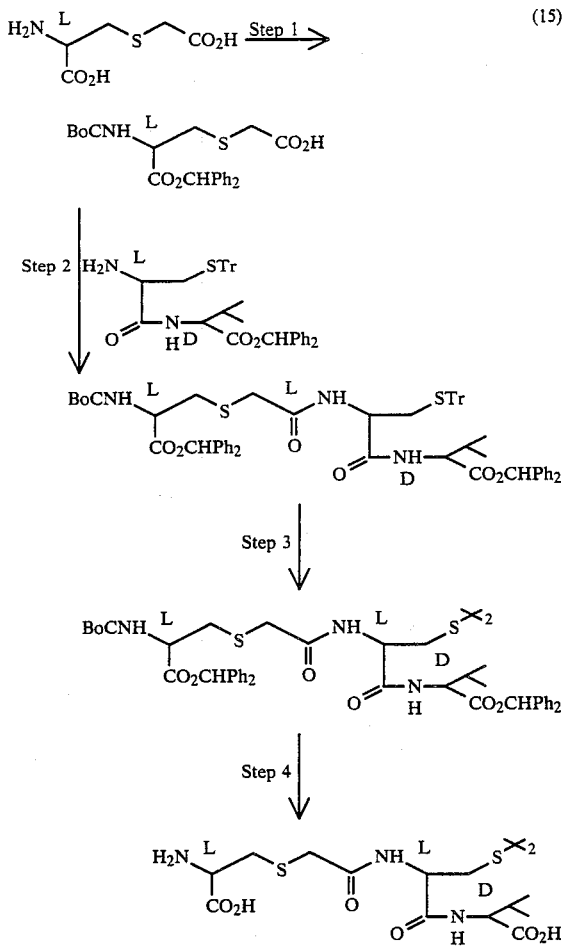

(15)

EXAMPLE 1

(a) Production of protected L-carboxymethylcysteine from L-carboxymethylcysteine.

A mixture of L-carboxymethylcysteine (1.0 g, 5.6 mmoles) and p-toluenesulfonic acid hydrate (1.12 g, 5.88 mmoles) was dissolved in water (10 mL), with heating, and the solvent was removed under reduced pressure. The salt (1.06 g, 3 mmoles) was dissolved in dimethylformamide (DMF) 3 mL) and, at 40° C., a solution of diphenyldiazomethane (0.58 g, 3 mmoles) in DMF (2 mL) was added dropwise with stirring. Stirring was continued for 5 min after the addition was complete, and the solution was then cooled to 30° C., and a solution of sodium acetate (800 mg) in water (4 mL) was added dropwise with stirring. Crystallization occurred during this addition. The mixture was maintained at 4° overnight, and the product was then collected, washed with water and then with ether, and dried: 382 mg, m.p. 141°–143°.

The ester (172.5 mg, 0.5 mmole) was suspended in methanol (2 mL), and dicyclohexylamine (0.1 mL, 0.525 mmole) was added, with stirring. When a clear colorless solution had been obtained (20 min), BOC-ON ® (Aldrich Chemical Company) 130 mg, 0.525 mmole) was added, and stirring was continued. After 24 hr, the solvent was removed, and the white foam was dissolved in ether (5 mL). This solution was washed successively with 5% sodium bicarbonate (2×5 mL), water (1×5 mL), 10% potassium bisulfate (2× mL), and brine (1×5 mL), and dried. After removal of the solvent the residue was triturated with hexane, and recrystallized twice from ether-petroleum ether to give white crystals, 102.4 mg, m.p. 77.5°–79.0°; tlc (CHCl$_3$-methanol, 9:1) R$_f$=0.2; IR (KBr): 3350, 1730, 1700, 1670 cm$^{-1}$; nmr (CDCl$_3$, δ): 1.41 (9H, s), 3.00–3.18 (4H, m), 4.68 (1H, m), 5.40 (1H br d, 9 Hz), 6.90 (1H, s), 7.33 (10H).

(b) Production of a fully protected tripeptide from protected L-carboxymethylcysteine.

The protected L-carboxymethylcysteine (98 mg, 0.22 mmole) was dissolved in methylene chloride (2 mL) and EEDQ ® (Aldrich Chemical Company) (59.3 mg, 0.24 mmole) was added. After 2 min, a solution of the protected dipeptide (138.3 mg, 0.22 mmole, in methylene chloride (2 mL), was added. The resulting solution was stirred at room temperature for 30 h. The solvent was then removed, and the residue dissolved in ethyl acetate (8 mL) and washed successively with 10% potassium bisulfate (3×8 mL), water (1×8 mL), saturated sodium bicarbonate (2×8 mL), water (1×8 mL) and saturated sodium chloride (1×8 mL), dried over magnesium sulfate and evaporated. The resulting white foam (0.2119 g), was purified by flash chromatography on Kieselgel 60 (20 g) using methylene chloride-ethyl acetate (15:1), to afford a white foam, 87.6 mg; nmr (CDCl$_3$, δ): 0.68 (3H, d, 6 Hz), 0.81 (3H, d, 6 Hz), 1.40 (9H, s), 2.16 (1H, m), 2.49–2.79 (2H, octet, 5.5, 7.9, 18 Hz), 2.82–3.03 (2H, m), 2.96 (2H, s), 4.00 (1H, m), 4.55 (2H, m), 5.60 (1H, br d, 6 Hz), 6.44 (1H, d, 9 Hz), 6.75 (1H, br d, 8 Hz), 6.86 (1H, s), 6.86 (1H, s), 7.20–7.44 (35H, m).

(c) Production of fully protected disulphide from fully protected tripeptide.

The fully protected tripeptide (40 mg, 0.034 mmole) was dissolved in methanol (1 mL), and pyridine (0.011 mL, 0.136 mmole) was added with stirring, followed by iodine (9.2 mg, 0.036 mmole) in methanol (1.5 mL), added dropwise. The mixture was left at room temperature for 30 min, by which time crystallization had taken place. The mixture was cooled in an ice-bath, and ice-cold 10% sodium bisulfite (3 mL) was added. The methanol was then removed under reduced pressure, and the mixture was extracted wih ethyl acetate. The organic phase was washed with brine (1×5 mL), dried and evaporated to a colorless oil (35 mg), which crystallized upon trituration with petroleum ether. Recrystallization from methanol (1 mL) yielded 17.4 mg, m.p. 153°–154° C.; tlc (CH$_2$Cl$_2$-ethyl acetate 9:1) R$_f$=0.73; nmr (CDCl$_3$, δ): 0.83 (3H, d, 7 Hz), 0.89 (3H, d, 7 Hz), 1.40 (9H, s), 2.28 (1H, m), 2.87–3.12 (6H, m), 4.61 (2H, q, 5, 8 Hz), 5.52 (2H, m), 6.86 (1H, s), 6.90 (1H, s), 7.30 (20H, m), 7.43 (1H, d, 8 Hz), 8.29 (1H, d, 9 Hz).

(d) Preparation of the deprotected tripeptide δ-(L-carboxymethylcysteinyl)-L-cysteinyl-D-valine (SCV) from the fully protected disulfide.

A solution of the fully protected disulfide (15 mg) in 98% formic acid (5 mL) was stirred overnight and then freeze-dried. The residue was partitioned between water (3 mL) and ether (3 mL). The aqueous phase was washed with ether (2×3 mL) and freeze-dried to give the deprotected tripeptide, 9 mg; tlc (methyl ethyl ketone-water-acetic acid 4:1:1) R$_f$=0.1; nmr (D$_2$O, δ): 0.95 (6H, br t), 1.24 (1H, br t), 2.99–3.28 (4H, m), 3.44 (2H, s), 3.98 (1H, q, 6, 8 Hz), 4.35 (1H, d, 9 Hz), 4.82 (1H, m).

EXAMPLE 2

Conversion of ACV and SCV into their respective penicillins by the partially purified cyclase enzyme of *S. clavuligerus*.

(a) Cyclization of ACV.

To 0.4 ml of reaction mixture were added 0.6 mM of ACV dimer, 50/0 mM Tris-HCl pH 7.0 buffer and a mixture of the three enzymes from a cell-free extract of *S. clavuligerus*, as described in more detail in U.S. application Ser. No. 410,302, now U.S. Pat. No. 4,510,246, together with 45.0 μM ferrous sulfate and 2.8 mM ascorbic acid as optimized amounts of essential co-factors. DTT was added in excess of the amount required to reduce ACV dimer to ACV monomer. The reaction was continued for approximately 2 hours at 20° C. and then terminated by addition of 0.4 ml methanol to precipitate protein. It was found, by bioassay and HPLC procedures (described in more detail hereinafter) that the peptide had been converted to a mixture of isopenicillin N and penicillin N. Ring expansion to a cephalosporin did not occur. The experiment was repeated with the addition of 1 mM of a standard oxygenase type enzyme co-factor, alphaketoglutarate, and in this case it was found that the ACV was converted to desacetoxycephalosporin C.

(b) Cyclization of SCV

Example 2(a) above was repeated using SCV (15) as the starting material.

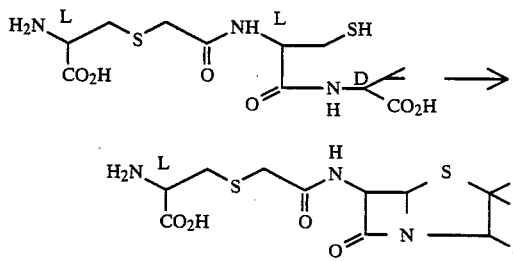

Antibiotic in reaction mixtures was estimated by the agar diffusion method. Cyclization reaction mixtures were bioassayed using *Micrococcus lutens* ATCC 9341 and *Escherichia coli* Ess as indicator organisms. Ring expansion reaction mixtures were bioassayed using *E. coli* Ess as indicator organism in agar plates supplemented with penicillinase at $2 \times 10^5$ units/ml.

High Performance Liquid Chromatography (HPLC)

Methanol inactivated reaction mixtures were centrifuged at 12,000xg for 5 min to remove precipitated protein before analysis. The chromatographic equipment used was: M-6000A pump, UK-6 injector, M-480 variable wavelength detector, M-420 data module and Bondapak-C18 column (rad Pak A in a Z module) as stationary phase. All equipment was from Waters Scientific Co., Mississauga, Ontario. The mobile phase consisted of methanol/0.05M potassium phosphate buffer, pH 4.0. The methanol content of the mobile phase depended upon the particular separation. A short precolumn (packed with Bondapak $C_{18}$/Corasil) was used to guard the main column. UV-absorbing material was detected at 220 nm at a sensitivity of 0.02 AUFS.

The substrates were employed at a concentration of 200 μg/0.4 mL of reaction mixture. In HPLC assays, the natural peptide ACV is observed at 20.86 min, and isopenicillin N, the natural product of the cyclization reaction, is observed at 4.60 min. With the unnatural precursor SCV, the corresponding retention times are: SCV, 20.90 min; penicillin, 5.33 min. Bioassay data are summarized in the following Table.

| Sample | Time of Incubation (h) | Zone of Inhibition (mm) *M. luteus* | *E. coli* Ess |
|---|---|---|---|
| No enzyme control | | 0.0 | 0.0 |
| ACV | 0.25 | 18 | halo |
| SCV | 0.25 | 10.5 | halo |
| ACV | 1.0 | 23 | halo |
| SCV | 1.0 | 22 | halo |

EXAMPLE 3

Conversion of SCV into a mixture of δ-(L-Carboxymethylcysteinyl)- and δ-(D-Carboxymethylcysteinyl)-penicillins by an Enzyme Extract from Streptomyces Clavuligerus which Contains Cyclase and Epimerase This experiment employs the salt-precipitated cell-free extract and cyclization assay prepared as follows:

Production of SPCFX (a) Culture of *S. clavuligerus*

*Streptomyces clavuligerus* NRRL 3585 was maintained on a sporulation medium composed of tomato paste 20 g; oatmeal, 20 g; agar, 25 g, in 1 liter of distilled water, pH 6.5

Inoculated plates were incubated 7–10 days at 28° C. Spores were scraped off into sterile distilled water (5 ml/plate) and used to inoculate, 2% v/v, 25 ml/125 ml flask, seed medium of the following composition: glycerol, 10 ml; sucrose, 20 g; soy flour, 15 g; yeast extract, 1 g; tryptone, 5 g; $K_2HPO_4$, 0.2 g in 1 liter of distilled water, pH 6.5. Inoculated seed medium was incubated 3 days and used to inoculate, 2% v/v, 100 ml amounts of production medium in 500 ml flasks. Production medium consisted of soluble starch, 10 g; L asparagine, 2 g; 3-N-morpholinopropane-sulfonic acid, 21 g; $MgSO_4.7H_2O$, 0.6 g; $K_2HPO_4$, 4.4 g; $FeSO_4.7H_2O$, 0.01 mg; $MnCl_2.4H_2O$, 0.01 mg; $ZnSO_4.7H_2O$, 0.1 mg; and $CaCl_2.2H_2O$, 0.013 mg in 1 liter of $H_2O$, pH 6.8. Inoculated production medium was incubated 40–48 h and the cells were then collected by filtration and used to prepare cell-free extracts. All incubations were at 27° C. on a gyrotory shaker (250 rpm, 19 mm eccentricity).

(b) Preparation of Cell-Free Extracts

Cell-free extracts were prepared by washing 40–48 h cells of *S. clavuligerus* in 0.05M Tris-HCl buffer, pH 7.0+0.1 mM dithiothreitol (DTT) (100 ml/100 ml culture). Washed cells were resuspended to 1/10 of the original culture volume in the same buffer and disrupted by sonication in an ice water bath for $2 \times 15$ sec at maximum intensity (300 watts, Biosonik III, Bronwill Scientific). Broken cell suspensions were centrifuged 1 h at 100,000xg. All cell-free extracts were stored frozen at −20° C.

Salt-precipitated cell-free extract was prepared by gradual addition of streptomycin sulfate to cell-free extract with gentle stirring at 4° C. to a final concentration of 1%, w/v. After 15 min at 4° C., precipitated nucleic acid was removed by centrifugation for 15 min at 15,000xg. Solid ammonium sulfate was then gradually added to the supernatant with gentle stirring at 4° C. until 40% saturation was reached. After 15 min at 4° C. the suspension was centrifuged as above and the pellet discarded. Additional ammonium sulfate was then added to the supernatant, as above, until 70% saturation was reached. Following centrifugation, the pellet was resuspended to its original volume in 0.05M Tris-HCl buffer pH 7.0 containing 0.1 mM DTT. The enzyme solution was then concentrated to 1/10 of the original volume by ultrafiltration with Amicon®PM-10 filter.

Cyclization Assay System

Cyclization activity of enzyme preparations was measured in reaction mixtures containing: bis-δ-(L-α-aminoadipyl-L-cysteinyl-D-valine) $(ACV)_2$ 0.306 mM, DDT 4 mM, Na ascorbate, 2.8 mM, $FeSO_4$ 45 μM, tris-HCl buffer 0.05M, pH 7.0, enzyme preparation 0.03-0.3 ml, final volume 0.4 ml. Reaction mixtures were incubated at 20° C. for up to 4 hours and stopped by cooling on ice or by the addition of 0.4 ml methanol.

In HPLC assays, the natural (ACV) peptide precursor is seen to be converted to an inseparable mixture of isopenicillin N and penicillin N at 4.60 min. However, the unnatural peptide SCV is converted to the isopenicillin N analog, at 5.33 min, and the penicillin N analog, at 4.53 min. Bioassay data are summarized in the following Table:

| Sample | Time of Incubation (h) | Zone of Inhibition (mm) M. luteus | E. coli Ess |
|---|---|---|---|
| No substrate control | | 0.0 | 0.0 |
| ACV | 0.25 | 23 | 25 |
| SCV | 0.25 | 16 | 19 |
| ACV | 1.0 | 28.5 | 26 |
| SCV | 1.0 | 23.5 | 25 |

EXAMPLE 4

Conversion of SCV into δ-(D-Carboxymethylcysteinyl)desacetoxy- and δ-(D-Carboxymethylcysteinyl)desacetylcephalosporins by an Enzyme Extract from Streptomyces Clavuligerus which Contains, Cyclase, Epimerase, Ring Expansion and Hydroxylase Enzymes

SCV ⟶

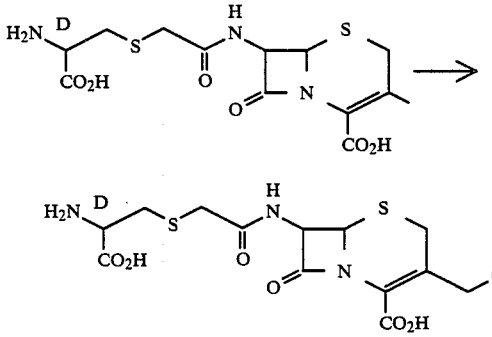

This experiment employs the salt-precipitated cell-free extract described in Example 3 and a similar ring expansion assay system using the cyclization assay system described above but supplemented with ATP 0.5 mM, α-ketoglutarate 1 mM, KCl 7.5 mM, and $MgSO_4$ 7.5 mM. Total volume and incubation conditions were the same as for the cyclization assay. The HPLC assay is described in S. E. Jensen, D. W. S. Westlake and S. Wolfe, Antimicrobial Agents and Chemotherapy Vol. 24, p. 307 (1983). In addition to HPLC and bioassay, reaction mixtures were spotted on a tlc sheet, developed in butanol-acetic acid-water (3:1:1) and bioassayed versus E. coli Ess.

After 2 h, the tlc assay with the natural peptide ACV as the precursor shows penicillin N at $R_f=0.54$, desacetoxycephalosporin C at $R_f=0.41$ and desacetylcephalosporin C at $R_f=0.28$. Beginning with the unnatural peptide SCV, the corresponding zones are seen after 2 h at $R_f=0.53$, 0.39 and 0.23, respectively. The HPLC assays beginning with SCV show the desacetoxycephalosporin at 9.46 min, and the desacetylcephalosporin at 4.03 min. The results of bioassay are summarized in the following Table:

| Sample | Incubation Time (h) | Zone of Inhibition (versus E. coli, mm) No Penicillinase | With Penicillinase |
|---|---|---|---|
| no substrate control | 1.0 | 0.0 | 0.0 |
| no substrate control | 2.0 | 0.0 | 0.0 |
| ACV | 1.0 | 24 | 24 |
| SCV | 1.0 | 22.5 | 16 |
| ACV | 2.0 | 25.5 | 25.5 |
| SCV | 2.0 | 24 | 22.5 |

EXAMPLE 5

Conversion of δ-(L-Carboxymethylcysteinyl)penicillin into δ-(D-Carboxymethylcysteinylpenicillin The penicillin substrate was synthesized chemically, from 6-aminopenicillanic acid, by a modification of the procedure reported in Journal of Antibiotics, Volume 29, page 1258 (1976). Exposure of the penicillin to epimerase, as described in Example 3, led to the penicillin N analog δ-(D-carboxymethylcysteinyl)penicillin, identified by HPLC and bioassay.

EXAMPLE 6

Ring Expansion of δ-(D-Carboxymethylcysteinyl)-penicillin to the Desacetoxycephalosporin Compound The penicillin substrate was synthesized chemically, from 6-aminopenicillanic acid, bromoacetic acid and D-cysteine, as described in Journal of Antibiotics, Volume 29, page 1258 (1976). Exposure of the penicillin to the ring expansion enzyme, as described in Example 4, led to the desacetoxycephalosporin, identified by tlc assay, by HPLC and by bioassay.

EXAMPLE 7

Conversion of δ-(D-Carboxymethylcysteinyl)-desacetoxycephalosporin to δ-(D-Carboxymethylcysteinyl)desacetylcephalosporin The cephalosporin substrate was synthesized chemically from 7-ADCA, bromoacetic acid and D-cysteine, and exposed to the hydroxylase enzyme, as described in Example 4. The desacetylcephalosporin product was identified by tlc assay, by HPLC assay, and by bioassay.

EXAMPLE 8

Continuous Conversion of SCV into δ-(L-Carboxymethylcysteinyl)penicillin, δ-(D-carboxymethylcysteinyl)penicillin, δ-(D-Carboxymethylcysteinyl)-desacetoxycephalosporin, and δ-(D-Carboxymethylcysteinyl)desacetylcephalosporin on an Immobilized Enzyme Reactor This experiment employs SCV as substrate, salt-precipitated cell-free extract from S. clavuligerus as the enzyme source, immobilized on a DEAE-trisacryl resin. Sequential conversion of the peptide to the isopenicillin N analog, the penicillin N analog, the desacetoxycephalosporin analog and the desacetylcephalosporin analog was observed.

(a) Preparation of Cell-Free Extracts for Immobilization

Cell-free extracts were prepared by washing 40-48 h cells of *S. clavuligerus* in 0.05M Tris-HCl buffer, pH 7.0+0.1 mM dithiothreitol+0.01 mM ethylenediaminetetracetic acid (EDTA buffer) (100 ml/100 ml culture). Washed cells were resuspended to 1/10 of the original culture volume in EDTA buffer and disrupted by sonication in an ice water bath for $2 \times 15$ sec at maximum intensity (300 watts, Biosonik III, Bronwill Scientific). Broken cell suspensions were centrifuged 1 h at 100,000xg. All cell-free extracts were stored at $-20°$ C.

Salt-precipitated cell-free extract was prepared by gradual addition of streptomycin sulfate to cell-free extract with gentle stirring at 4° C. to a final concentration of 1%, w/v. After 15 min at 4° C., precipitated nucleic acid was removed by centrifugation for 15 min at 15,000xg. Solid ammonium sulfate was then gradually added to the supernatant with gentle stirring at 4° C. until 40% saturation was reached. After 15 min at 4° C. the suspension was centrifuged as above and the pellet discarded. Additional ammonium sulfate was then added to the supernatant, as above, until 70% saturation was reached. Following centrifugation, the pellet was resuspended to its original volume in EDTA buffer. The enzyme solution was then concentrated to 1/10 of the original volume by ultrafiltration with an Amicon ®PM-10 filter.

(b) Immobilization of Salt-Precipitated Cell-Free Extract

DEAE-trisacryl resin was loaded into a column 0.4×5.8 cm (packed bed volume, 1 ml), washed with 3×2 ml of the same EDTA buffer, and allowed to drain to dryness by gravity. One milliliter of the salt-precipitated cell-free extract above was applied to the column. The effluent was collected and reapplied to the column twice to ensure complete enzyme loading. The column was washed with 2×1 ml of the same EDTA buffer, drained dry and centrifuged for 3 min. at 500xg to remove excess buffer. This immobilized enzyme reactor was stored at 4° C. when not in use.

The penicillin and cephalosporin-forming ability of the immobilized enzyme reactor as prepared above was demonstrated using reaction mixtures containing: (SCV)$_2$ or (ACV)$_2$ 0.306 mM, dithiothreitol 4 mM, Na ascorbate 2.8 mM, FeSO$_4$ 45M, $\alpha$-ketoglutarate 1 mM, KCl, 7.5 mM, MgSO$_4$ 7.5 mM, in TDE buffer, final volume 2.0 ml.

2 ml of the reaction mixture was applied to the immobilized enzyme reactor by means of a peristaltic pump operating at 40 ml/h. Effluent was collected into a 13×100 mm test tube from which the original reaction mixture was pumped, and therefore was recycled continuously through the enzyme reactor. In the case of (ACV)$_2$ the enzyme reactor was operated at 21° C. and 20 μl aliquots were removed at 15 minute time intervals for analysis for antibiotic formation. (Table).

TABLE
BIOASSAY OF REACTION MIXTURES

| Sample Time (min) | Zone of Inhibition (mm) | Cephalosporin C* "equivalents" (μg) |
|---|---|---|
| 0 | 0 | 0 |
| 15 | 15 | .031 |
| 30 | 19.5 | .086 |
| 45 | 18.5 | .062 |
| 60 | 21.5 | .136 |
| 75 | 21.5 | .136 |

*One microgram of cephalosporin C "equivalent" gives a zone of inhibition equal to that produced by 1 μg of actual cephalosporin C.

Antibiotic levels increased for 60 min. before leveling off. Since the bioassays were performed in the presence of penicillinase, the antibiotic activity detected was due to cephalosporin antibiotics only. We have previously shown that cephalosporins can also arise from ACV or SCV via the production of the penicillin intermediates, isopenicillin N and penicillin N. The immobilized enzyme reactor similarly must form cephalosporins by the sequential cyclization, epimerization and ring expansion of the ACV or SCV peptide substrates.

Based on these studies we conclude that the immobilized enzyme reactor is converting ACV or SCV via a multi-step reaction involving penicillin intermediates into cephalosporin products.

EXAMPLE 9

Oral Absorption of Carboxymethylcysteinyl-Desacetoxycephalosporin C

Three male Spague-Dawley rats were starved overnight. Antibiotic solutions (10 milligrams per milliliter in water) were administered by oral lavage at a rate of 20 milligrams per kilogram body weight as follows:

| Rat Number | Weight | Antibiotic Administered |
|---|---|---|
| 1 | 322 grams | Sodium Cephalosporin C 0.64 milliliters |
| 2 | 320 grams | CmC—DaO—C 0.64 milliliters |
| 3 | 322 grams | Cmc-DaO—C 0.64 milliliters |

One hour after the antibiotics were administered blood was collected from the rats into sterile citrate containing syringes. Blood samples were centrifuged to sediment red blood cells and 20 micro liter amounts of plasma were bioassayed in duplicate using Escherichia Coli. ess. as the indicator organism. Original antibiotic solutions were also diluted and bioassayed in duplicate.

| Sample ( 20 Milliliters) | Zone of Inhibition (milimeters) |
|---|---|
| Plaza-Rat 1 | 0,0 |
| Plaza-Rat 2 | 18.5, 18.5 |
| Plaza-Rat 3 | 8.5, 8.5 |
| Na—Ceph-C (10 micrograms per milliliter) | 23.5, 23.5 |
| Na—Ceph-C (1 microgram per milliliter) | 8,8 |
| Cmc-DaO—C (10 micrograms per milliliter) | 33, 33 |
| Cmc-DaO—C (1 microgram per milliliter) | 17.5, 17.0 |

In vitro antibacterial activity was compared by standard procedures. The minimum inhibitory concentrations were tabulated in the following table:

TABLE

IN VITRO ANTIBACTERIAL ACTIVITY (MICROGRAMS/ML)

| ORGANISM | (a) | (b) | (c) | (d) | (e) | (f) |
|---|---|---|---|---|---|---|
| E. COLI ESS | 0.2 | 3 | 0.04 | 0.6 | 0.1 | 0.22 |
| E. COLI B | >20 | >30 | 47 | 12 | 50 | 80 |
| S. TYPH. | >20 | >30 | 12 | 10 | 10 | 0.8 |
| COMAMONAS TERRIGENA | 2 | 30 | 0.24 | 6.2 | 1 | 0.42 |
| M. LUTEUS | 10 | 16 | 4.7 | 0.25 | 10 | 0.04 |
| S. AUREUS N[2] (PEN RESIST.) | >20 | | 30 | 47 | 2.5 | 100 | 8 |
| PS. AERUGINOSA | — | — | — | — | — | — |

(a) DESACETOXY C
(b) DESACETOXY-L
(c) DESACETOXY-D
(d) CEPHALEXIN
(e) CEPH C
(d) D-CMC-CEPH C

For ready reference, the structural formulae of the above compounds (a)-(f) are tabulated on the following page.

DESACETOXY C (a)

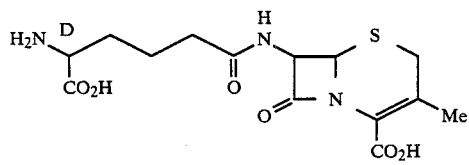

DESACETOXY-L (b)

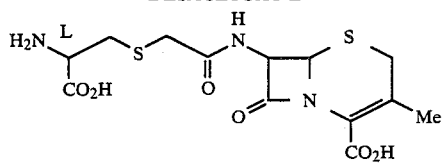

DESACETOXY-D (c)

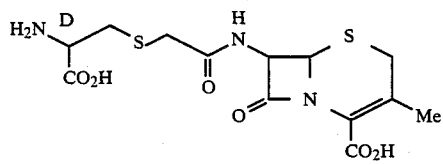

CEPHALEXIN (d)

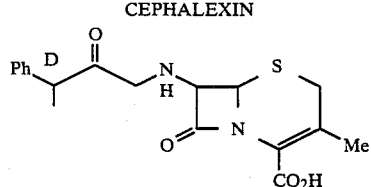

CEPH C (e)

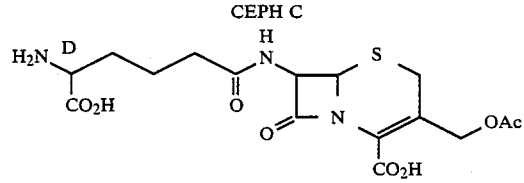

D-CMC—CEPH C

-continued (f)

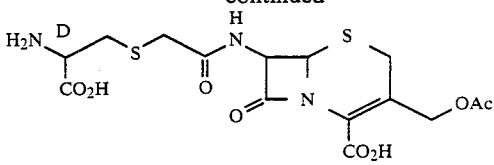

It will be appreciated that compound (c) is described in Example 9 as orally absorbed in rat, compound (d) is an important commercial antibiotic which is orally absorbed and compound (e) is an antibiotic which is not orally absorbed.

We claim:

1. A process for producing a penicillin of the formula:

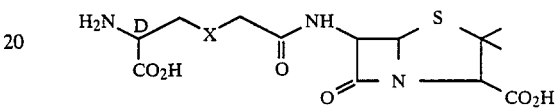

where X=S, SO, $SO_2$, O, NH, NR, PO, PR, Se, SeO or $SeO_2$ and R=alkyl or aryl which comprises reacting a peptide starting material having the formula:

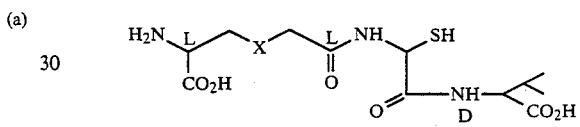

where X and R are as above defined with cyclase and epimerase enzymes isolated from a cell-free extract of a prokaryotic β-lactam producing organism for sufficient time and in the presence of sufficient co-factors to provide said penicillin, and recovering said penicillin therefrom.

2. A process for producing a cephalosporin of the formula:

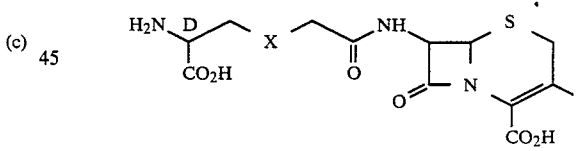

where X=S, SO, $SO_2$, O, NH, NR, PO, PR, Se, SeO or $SeO_2$ and R=arkyl or aryl which comprises reacting a peptide starting material having the formula:

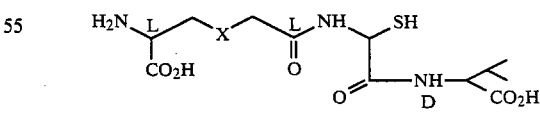

where X and R are as above identified with cyclase, epimerase and a ring expansion enzyme isolated from a cell-free extract of a prokaryotic β-lactam producing organism for sufficient time and in the presence of α-ketoglutarate, ferrous ion and ascorbate as co-factors so as to produce said cephalosporin, and recovering the cephalosporin therefrom.

3. A process for producing a cephalosporin of the formula:

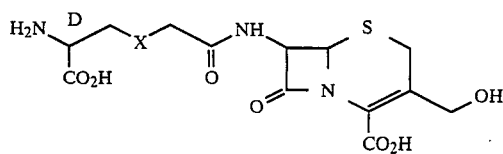

where X=S, SO, SO$_2$, O, NH, NR, PO, PR, Se, SeO or SeO$_2$ and R=alkyl or aryl which comprises reacting a peptide starting material having the formula:

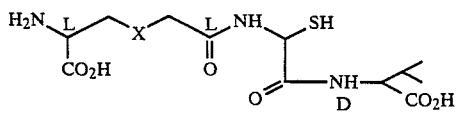

where X and R are as above defined with cyclase, epimerase, ring expansion enzyme and hydroxylase isolated from a cell free extract of a prokaryotic β-lactam producing organism for sufficient time and in the presence of α-ketoglutarate, ferrous ion and ascorbate as co-factors so as to produce said cephalosporin, and recovering said cephalosporin therefrom.

4. A process as claimed in claim 1 wherein X is S.
5. A process as claimed in claim 2 wherein X is S.
6. A process as claimed in claim 3 wherein X is S.
7. A process as claimed in claim 1 wherein said prokaryotic β-lactam producing organism is selected from the group comprising S. clavuligerus, S. cattleya and S. lipmanii.
8. A process as claimed in claim 2 wherein said prokaryotic β-lactam producing organism is selected from the group comprising S. clavuligerus, S. cattleya and S. lipmanii.
9. A process as claimed in claim 3 wherein said prokaryotic β-lactam producing organism is selected from the group comprising S. clavuligerus, S. cattleya and S. lipmanii.
10. A process for producing an analog of penicillin-N having the formula:

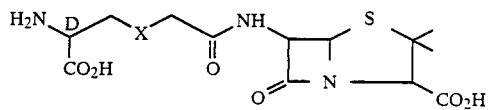

where X=S, SO, SO$_2$, O, NH, NR, PO, PR, Se, SeO or SeO$_2$ and R=alkyl or aryl comprising reacting an analof of isopenicillin-N having the formula:

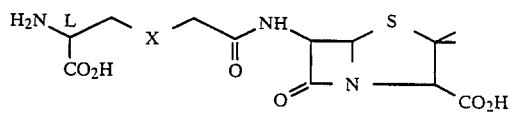

where X and R are as above defined with the epimerase and ring expansion enzyme isloated from a cell free extract of a prokaryotic cephalosporin producing organism.

11. A process as claimed in claim 10 wherein said prokaryotic organism is selected from the group comprising S. clavuligerus, S. cattleya and S. lipmanii.
12. A process as claimed in claim 11 wherein X is S.
13. A process for providing cephalosporins of the formula

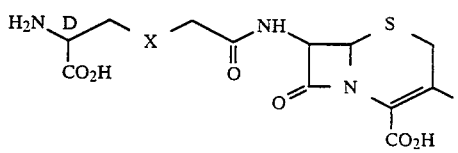

where X=S, SO, SO$_2$, O, NH, NR, PO, PR, Se, SeO or SeO$_2$ and R=alkyl or aryl which comprises reacting an analog of isopenicillin-N having the formula

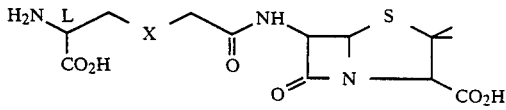

where X and R are as above defined, with epimerase and a ring expansion enzyme isolated from a cell free extract of a prokaryotic cephalosporin-producing organism.

14. A process as claimed in claim 13 wherein X is S.

* * * * *